United States Patent [19]

Inaba

[11] Patent Number: 4,662,381

[45] Date of Patent: May 5, 1987

[54] METHOD OF COLLECTING A SAMPLE OF ENDOMETRIUM CELLS

[76] Inventor: Yushihiko Inaba, 4-5, Matsushima 4 chome, Edogawa-ku, Tokyo, Japan

[21] Appl. No.: 755,096

[22] Filed: Jul. 15, 1985

Related U.S. Application Data

[62] Division of Ser. No. 527,819, Aug. 30, 1983, abandoned.

[30] Foreign Application Priority Data

Nov. 2, 1982 [JP] Japan ................................ 57-191761

[51] Int. Cl.$^4$ .............................................. A61B 10/00
[52] U.S. Cl. .................................................... 128/756
[58] Field of Search ........................ 128/749, 756–757, 128/772, 357, 1 R

[56] References Cited

U.S. PATENT DOCUMENTS

| | | | |
|---|---|---|---|
| 2,955,591 | 10/1960 | MacLean | 128/756 |
| 3,777,743 | 12/1973 | Binard et al. | 128/749 |
| 3,796,211 | 3/1974 | Kohl | 128/749 |
| 3,881,464 | 5/1975 | Levene | 128/756 |
| 4,227,537 | 10/1980 | Suciu et al. | 128/756 |
| 4,235,245 | 11/1980 | Naito | 128/756 |
| 4,245,653 | 1/1981 | Weaver | 128/756 X |

FOREIGN PATENT DOCUMENTS

80/01353  7/1980  PCT Int'l Appl. ................. 128/756

*Primary Examiner*—Edward M. Coven
*Attorney, Agent, or Firm*—Birch, Stewart, Kolasch & Birch

[57] ABSTRACT

A method of collecting a sample of endometrium cells from the uterus of a subject. A collector is used which has an outer tube member formed with an inward portion at least an inward end part of which is flexible, and a substantially coaxial outward portion axially abutted thereto. A rod member is passed at least partly through the central hole of the tube member, and is formed with an inward portion at least an inward end part of which is flexible, and a substantially coaxial outward portion axially abutted thereto. A means for collecting endometrium cells is provided on the inward portion of the rod member near its free end, and a means is provided for biasing the rod member with respect to the tube member in the outward direction. A stop means is provided for preventing the rod member from moving with respect to the tube member in the outward direction past a first certain point at which the endometrium cell collecting means is completely housed within the inward portion of the tube member, and another stop means is provided for preventing the rod member from moving with respect to the tube member in the inward direction past a second certain point at which the endometrium cell collecting means projects from the free end of the inward portion of the tube member. A means may be provided, optionally, for limiting the movement of the tube member in the inward direction into the uterine os of the subject. The collector is inserted into the cervix and a force is applied to the collector to reciprocate the rod member in the tube member in the inward and outward directions. The force being affected by the biasing means and projecting the endometrium cell collecting means from the tube member. Withdrawing the endometrium cell collecting means into the tube member and then withdrawing the collector from the cervix.

1 Claim, 9 Drawing Figures

METHOD OF COLLECTING A SAMPLE OF ENDOMETRIUM CELLS

This application is a divisional of copending application Ser. No. 527,819, filed on Aug. 30, 1983, abandoned.

BACKGROUND OF THE INVENTION

The present invention relates to an endometrium cell sample collector for taking samples of endometrium tissue for the diagnosis of cancer and the like, and more particularly relates to such an endometrium cell sample collector, which is easily operable and can be made so cheaply as to be disposable.

Uterine cancer in general falls into two categories: cervical cancer which develops in the cervix, and endometrial cancer which develops in the endometrium. Cervical cancer may be diagnosed by observing the cervix by using a colposcope, but the diagnosis of endometrial cancer is difficult, and generally it is required to take a sample of the endometrium cells for laboratory testing.

For taking such a endometrium cell sample, a call sample collector is required, and in the past generally a suction type cell sample collector has been used, which takes a sample of the endometrium cell tissue by sucking it away from the endometrium. However, such a conventional endometrium cell sample collector is not entirely satisfactory, since because there is little air in the uterine cavity in the beginning, when suction is performed, the pressure difference between the uterine cavity and the interior of the cell sample collector tends to quickly disappear, no matter how vigorously the suction action is performed, and thus the suction action thereof cannot be very effective. Thus cell collection for endometrial cancer detection becomes difficult. Further, the need for constructing such an endometrium cell sample collector with a suction capability requires high manufacturing accuracy which entails high manufacturing cost, and thus if the endometrium cell sample collector is intended to be disposable then it is expensive during use, while on the other hand if the endometrium cell sample collector is intended to be reused for taking cell samples several times then problems arise with regard to cleaning, sterilization, and the like thereof.

Another requirement for such an endometrium cell sample collector of course is that it should be quite safe to use, and should be effective for collection of endometrium cell tissue. Since the interior of the uterus is accessible only via the cervix, which is rather restricted, it is important and problematic, first of all not to damage the cervix during removal of the endometrium cell sample, and also not to mix any cervical tissue cells in with the sample of endometrium cells which is being extracted from the uterine cavity. These aims must be accomplished although the angle for passing via the cervix to the interior of the uterus may be rather awkward, at least in some subjects. Ease of use is another important requirement with regard to such an endometrium cell sample collector, and to this end it is desirable that it should be possible to operate it with only one hand.

SUMMARY OF THE INVENTION

The present inventor conceived of an endometrium cell sample collector which satisfied at least in part some of these requirements, and, in Japanese Utility Model Application Ser. No. 56-175526 (1981), which has been published as Japanese Utility Model Laying Open Publication Ser. No. 58-80208 (1983) and which was filed by the same inventor and applicant as the parent Japanese application of this present U.S. patent application of which priority is being claimed, has proposed an endometrium cell sample collector, comprising a flexible tube with an external uterine os contact portion provided at an intermediate part of this flexible tube so dimensioned as not to be passable past the external uterine os, a flexible cell sample collection rod which is fitted freely inside the flexible tube with a cell collection portion provided near its front or inner end adapted to remove a portion of the endometrium and to attach said portion to itself, and a stop which limits the distance to which the front or inner end of the collection rod can be projected out from the front end of the tube to a certain predetermined distance, the portion of the tube inward of the external uterine os contact portion being so dimensioned as to be insertable through the cervix and being of length approximately that of the cervix. Various refinements of this basic structure were also proposed by the present inventor in said above identified Japanese application and publication, which it is not intended to admit as prior art in this application. However, this structure is still not perfect, and in particular is not well adapted to being operated with one hand for taking an endometrium sample, since the axial reciprocation of the rod within the tube is required to be performed by holding the tube with one hand and the rod with the other hand. Also the removal of the endometrium sample from the device is not as convenient as could be desired; and other various problems during use can occur. Further, this device is not well adapted to the removal of an endometrium sample from a subject whose cervix is longer than the normal cervix, because in such a case the length of the aforesaid portion of the tube inward of the external uterine os contact portion may be insufficient.

Accordingly, it is the primary object of the present invention to provide an endometrium cell sample collector, which avoids the above mentioned disadvantages.

It is a further object of the present invention to provide such an endometrium cell sample collector, which can quickly and accurately collect an endometrium cell sample.

It is a further object of the present invention to provide such an endometrium cell sample collector, which does not operate by suction.

It is a further object of the present invention to provide such an endometrium cell sample collector, which can be easily operated with one hand.

It is a further object of the present invention to provide such an endometrium cell sample collector, which is easy to use.

It is a further object of the present invention to provide such an endometrium cell sample collector, which does not run any risk, during use, of damage to the cervix or the uterus.

It is a further object of the present invention to provide such an endometrium cell sample collector, which does not run any risk, during use, of contamination of the sample of endometrium cells taken thereby with any cells from the cervix.

It is a further object of the present invention to provide such an endometrium cell sample collector, which does not involve any difficulties with the angle for passing via the cervix to the interior of the uterus.

It is a further object of the present invention to provide such an endometrium cell sample collector, which is well adapted to the removal of an endometrium sample from a subject whose cervix is longer than the normal cervix.

It is further object of the present invention to provide such an endometrium cell sample collector, which aids with convenient removal of the endometrium sample which has been taken therewith.

It is a further object of the present invention to provide such an endometrium cell sample collector, which does not require to be cleaned for reuse.

It is a further object of the present invention to provide such an endometrium cell sample collector, which does not involve any problems with cleanliness or sterilization during use.

It is a further object of the present invention to provide such an endometrium cell sample collector, which is disposable.

It is a yet further object of the present invention to provide such an endometrium cell sample collector, which is cheap to manufacture.

It is a yet further object of the present invention to provide such an endometrium cell sample collector, the manufacture of which does not require any great production accuracy.

It is a yet further object of the present invention to provide such an endometrium cell sample collector, which is economical during use.

According to the most general aspect of the present invention, these and other objects are accomplished by a collector for collecting a sample of endometrium cells from the uterus of a subject, comprising: (a) a tube member, formed with a central axially extending aperture, and comprising an inward portion, with an inward free end, at least an inward end part of which including said inward free end thereof is flexible, and a substantially coaxial outward portion axially abutted thereto with a free end; (b) a rod member, which is passed at least partly through said central axially extending aperture of said tube member, comprising an inward portion, with an inward free end, at least an end part of which including said inward free end thereof is flexible, and a substantially coaxial outward portion axially abutted thereto with a free end; (c) a means for collecting endometrium cells, provided on said inward portion of said rod member near its said free end; (d) a means for biasing said rod member with respect to said tube member in the outward direction; (e) a means for preventing said rod member from moving with respect to said tube member in the outward direction past a first certain point at which said endometrium cell collecting means is completely housed within said inward portion of said tube member; and (f) a means for preventing said rod member from moving with respect to said tube member in the inward direction past a second certain point at which said endometrium cell collecting means projects from said free end of said inward portion of said tube member.

According to such an apparatus, when taking an endometrium cell sample, first the inward portion of the tube member is slipped into the uterine cervix of the subject, until the inward end thereof is slightly past the internal uterine os, and then the rod member is reciprocated in the tube member in the inward and outward directions, by a force being applied thereto which alternately respectively overcomes and is overcome by the biasing action of the biasing means, between its said first and second certain points with respect thereto, so as alternately to project said endometrium cell collecting means from the inward free end of the tube member so as to scrape endometrium cells off the wall of the uterine cavity of the subject, and to withdraw said endometrium cell collecting means into the inward portion of the tube member. Finally, after this reciprocation has been carried out an appropriate number of times, the device is withdrawn from the cervix, with at this time the rod member at its said frist point with respect to the tube member, so that the endometrium cell collecting means is at this time housed within the inward portion of the tube member, and so the endometrium cell sample thereon is protected from contamination by cervical cells. Thus, an endometrium cell sample is quickly and easily taken, without any reliance upon any suction effect as was the case in the above identified other Japenese patent application. Further, because of the provision of the biasing means for the rod member, this endometrium cell sample collector can be easily operated with one hand, and accordingly is very easy to use. Because this endometrium cell sample collector is very cheap to make, since its manufacture does not require any great production accuracy, it may be only used once and then thrown away, i.e. may be used disposably, and this means that it does not require cleaning before reuse, and accordingly problems with cleanliness or sterilization during use are obviated, and labor during use is saved, which further promotes economy during use. Further, if such a disposable method of use is being practiced, then after withdrawal from the body of the subject the rod member may be pushed against the biasing action of the biasing means so as to protrude the inward end of the rod member from the inward end of the tube member, and then the device may be bent through a sharp angle so as to fix for ever the rod member with respect to the tube member, which aids with the subsequent convenient removal of the endometrium sample which has been taken from the uterine cavity by adhesion to the means for collecting endometrium cells of this endometrium cell sample collector.

Further, according to a more particular aspect of the present invention, these and other objects are more particularly and concretely accomplished by such an endometrium sample collector as described above, furher comprising a means for limiting the movement of said tube member in the inward direction into the uterine cervix of the subject.

According to such an apparatus, the inward movement of the inward portion of the tube member into the uterine os of the subject may be at least gently stopped by this movement limiting means coming into contact with the external uterine os, just when the inward end thereof is slightly past the inner end of the internal uterine os, as appropriate.

Further, according to another more particular aspect of the present invention, these and other objects are more particularly and concretely accomplished by such an endometrium sample collector as first described above, wherein further said means for preventing said rod member from moving in the outward direction past said first certain point comprises a means for substantially sealing up said inward free end of said inward portion of said tube member so as to substantially completely house said endometrium cell collecting means therein.

According to such an apparatus, as the device is being withdrawn from the cervix, with the rod member at its said first point with respect to the tube member so that the endometrium cell collecting means is at this time housed within the inward portion of the tube member, in fact the endometrium cell collecting means is kept substantially sealed up in said inward portion of said tube member by said means for doing so, so as further to protect the endometrium cell sample thereon from contamination by cervical cells.

BRIEF DESCRIPTION OF THE DRAWINGS

The present invention will now be shown and described with reference to a preferred embodiment thereof, and with reference to the illustrative drawings. It should be clearly understood, however, that the description of the embodiment, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and features are denoted by like reference symbols in the various figures thereof, and:

FIG. 5, which consists of five

DESCRIPTION OF THE PREFERRED EMBODIMENT

Figure 1:
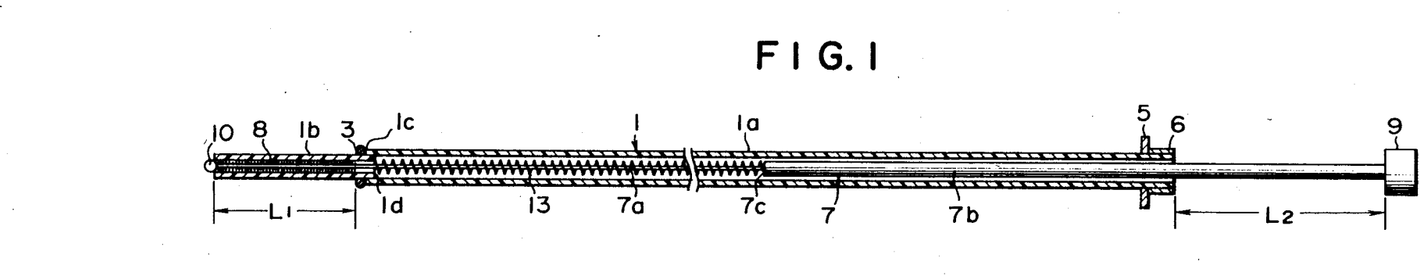
FIG. 1 is a sectional view of an endometrium cell sample collector which is the preferred embodiment of the endometrium cell sample collector of the present invention, taken in a plane which includes the longitudinal axis thereof.

The present invention will now be described with reference to the preferred embodiment thereof, and with reference to the appended drawings. FIG. 1 is a longitudinal sectional view of the preferred embodiment of the endometrium cell sample collector of the present invention. In the figures, the reference numeral 1 denotes generally a tube member 1, which is shown in side elevation in FIG. 2, and is the main structural member of the endometrium cell sample collector. The tube member 1 comprises a relatively long first tube portion 1a and a relatively short second tube portion 1b coaxial therewith and axially abutted thereto. In this preferred embodiment, the outer diameter of the first longer tube portion 1a is larger than the outer diameter of the second shorter tube portion 1b, so that an outer shoulder or step 1c is defined between the outer surfaces of the tube portions 1a and 1b; and also the inner diameter of the first longer tube portion 1a is larger than the inner diameter of the second shorter tube portion 1b, so that an inner shoulder or step 1d is defined between the inner surfaces of the tube portions 1a and 1b. The tube member 1 is made of an elastic synthetic resin, and is thus easily flexible, especially at its smaller diameter portion 1b.

Figure 2:
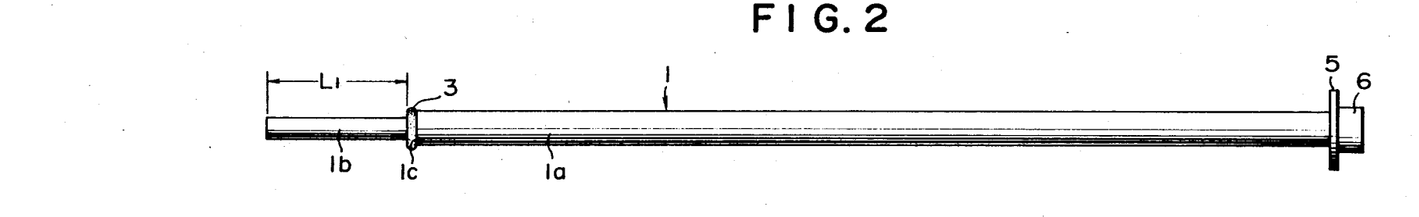
FIG. 2 is a side elevational view of a tube member which is a main member of said endometrium cell sample collector.

Over the smaller tube portion 1b there is fitted an elastic ring 3, which is made of a stretchable material such as rubber or a synthetic resin, and which is so dimensioned that, while it can be fairly easily slipped over the smaller tube portion 1b, it cannot at least without application of some force be slipped from said smaller tube portion 1b past the outer step 1c to fit over the larger tube portion 1a; and therefore, as a consequence of this, if said elastic ring 3 is so pushed over the larger tube portion 1a, it cannot thereafter slide thereon very easily, but is quite firmly fixed thereon with respect to the longitudinal direction. Thus the ring 3 is (during usual use of the device, as will be explained later) nestled against said outer step 1c on the outer surface of the tube member 1. As indicated in FIGS. 1 and 2, the distance between that end of the smaller tube portion 1b which is remote from the larger tube portion 1a and the side facing it of the ring 3, which is approximately equal to the total length of said smaller tube portion 1b, will be hereinafter referred to as $L_1$ in this specification. Further, over the end remote from the smaller tube portion 1b of the larger tube portion 1a there is fitted a flange 5, which serves as a finger grip member as will be seen hereinafter, and this finger grip member 5 is securely prevented from moving to the right in the figures relative to the larger tube portion 1a (which hereinafter in this specification will be referred to as the outward direction, in view of the method of use of this instrument for endometrium collection, to be explained later) by a collar 6 fitted at the end of said larger tube portion 1a and securely fixed to the outer surface of said tube portion 1a.

Figure 3:
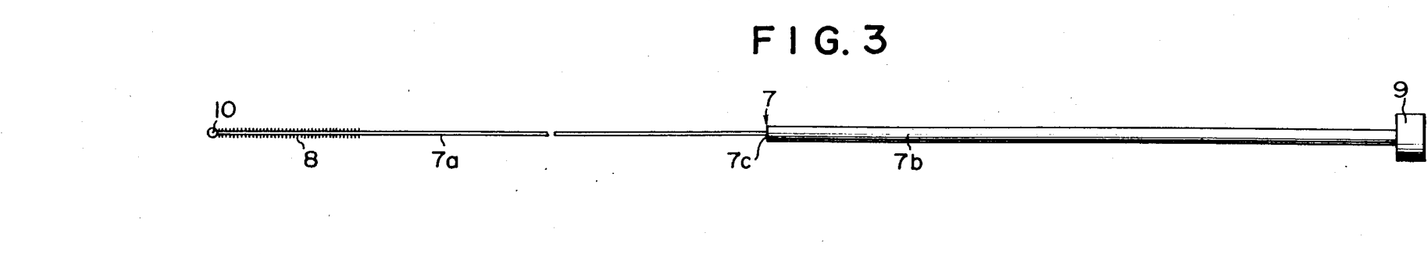
FIG. 3 is a side elevational view of a rod member which is fitted through said tube member, and is another main member of said endometrium cell sample collector.
Figure 4:
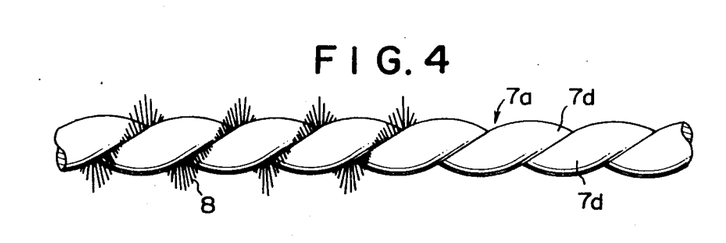
FIG. 4 is an enlarged side elevational view of a part of an end portion of said rod member, which is formed as a twisted wire type brush for cell collection.

Through the central longitudinal hole of the tube member 1 there is fitted a rod member 7, which is shown in side elevational view in FIG. 3. The rod member 7 comprises a first rod portion 7a and a second rod portion 7b coaxial therewith and axially abutted thereto. In this preferred embodiment of the endometrium cell sample collector of the present invention, the outer diameter of the first rod portion 7a is smaller than the outer diameter of the second rod portion 7b, so that a shoulder or step 7c is defined between the outer surfaces of the rod portions 7a and 7b. The smaller diameter rod portion 7a is relatively flexible, being made from a pair of stainless steel wires twisted together, as best shown in FIG. 4 which is an enlarged side elevational view of a part of the end portion 8 in the inward direction of said smaller diameter rod member 7a, and the larger diameter rod portion 7b is substantially not flexible, being made of aluminum alloy tube or the like.

As can be seen particularly in FIG. 4, in between the stainless steel wires of the inward end portion 8 of said smaller diameter rod portion 7a are wound and fixed whiskers of artificial fiber or the like, so that the end portion 8 of the rod member 7 is formed as a twisted wire type brush for endometrium cell collection as will be explained later. On the extreme inward end of said smaller diameter rod porton 7b (i.e., on the left end in the figures) there is fitted an outward motion stop 10, which in this preferred embodiment of the present invention is spherical and has a smooth surface and is of a diameter somewhat greater than the inner diameter of the smaller tube portion 1b. The outward end portion of the larger diameter rod portion 7b is provided with an inward motion stop 9, which also functions as a knob for being pressed by the thumb of an operator as will be explained hereinafter, and is of a diameter greater than the inner diameter of the larger tube portion 1a.

When the apparatus is assembled as shown in FIG. 1 (of course for the assembly procedure the outward motion step 10 is required to be removed from the inward end portion of the rod member 7), with the rod member 7 passed through the central hole of the tube member 1, a compression coil spring 13 is fitted within the central hole of the larger diameter portion 1a of the tube member 1, around the portion in the outward direction of the smaller diameter rod portion 7a, with the inward end of said compression coil spring 13 abutting against the aforesaid inner shoulder or step 1d defined between the inner surfaces of the larger and smaller diameter tube portions 1a and 1b, and the outward end of said compression coil spring 13 abutting against the aforesaid outer shoulder or step 7c defined between the outer surfaces of the larger and smaller diameter rod portions 7a and 7b. Thus, the biasing action of this compression coil spring 13 biases the rod member 7 as a whole in the rightward direction as seen in FIG. 1 with respect to the tube member 1, i.e. in the outward direction, so that, provided that no other force is applied to the apparatus, the rod member 7 is moved so far outwards relative to the tube member 1 that the outward motion stop member 10 is brought to abut against the inward end of the smaller diameter tube portion 1b, as shown in FIG. 1. In this position, the smaller diameter tube portion 1b, as shown in FIG. 1. In this position, the inward motion stop 9 at the outward end of the larger diameter rod portion 7b is moved to its maximum possible distance from the outward end of the larger tube portion 1a, and this distance will be hereinafter designated as $L_2$ in this specification, as indicated in FIG. 1; as will become apparent later, this distance is equal to the maximum stroke of the rod member 7 with respect to the tube member 1.

In FIGS. 5a to 5e, there are shown cross sectional views of a uterus and vagina and so on, with this device according to the preferred embodiment of the endometrium cell sample collector of the present invetion at various stages of taking an endometrium cell sample therefrom. Referring to these figures, now the use of this device for thus sampling the endometrium 19 in a uterine cavity 18 adhering to the inner surface of the uterus will be explained. In these figures, the reference numeral 11 denotes the internal uterine os of the cervix 2, while 12 is the fundus of the associated uterus; and 4 is the external uterine os, while 14 denotes the associated vagina. The dimensions of the parts of the device are approximately as follows, in this preferred embodiment of the present invention, with reference to a typical cervix and uterus. The outer diameter of the smaller tube portion 1b is such that said smaller tube portion 1b may be easily slipped through the external uterine os 4 of the average cervix 2, while the diameter of the elastic ring 3 is such that said ring 3 cannot be easily slipped into said average external uterine os 4. As for the outer diameter of the larger tube portion 1a, this is not critical, but for a reason to be explained later it is desirable that it should be such that said larger tube portion 1a may be without too much difficulty able to be slipped through the external uterine os 4, at least in the case of a cervix which is somewhat larger than the normal cervix. Further, the distance $L_1$ is slightly greater than the distance from the external uterine os 4 to the internal uterine os 11, i.e. the total length of the uterine cervix. And the distance $L_2$, i.e. the stroke of the rod member 7 with respect to the tube member 1, is approximately equal to the distance between the internal uterine os 11 and the uterus fundus 12. Therefore, the distance $L_1$ plus $L_2$ is approximately equal to the distance from the external uterine os 4 to the fundus 12 of the uterus.

This device is used as follows for sampling the endometrium 19 in the uterine cavity 18.

Figure 5A:
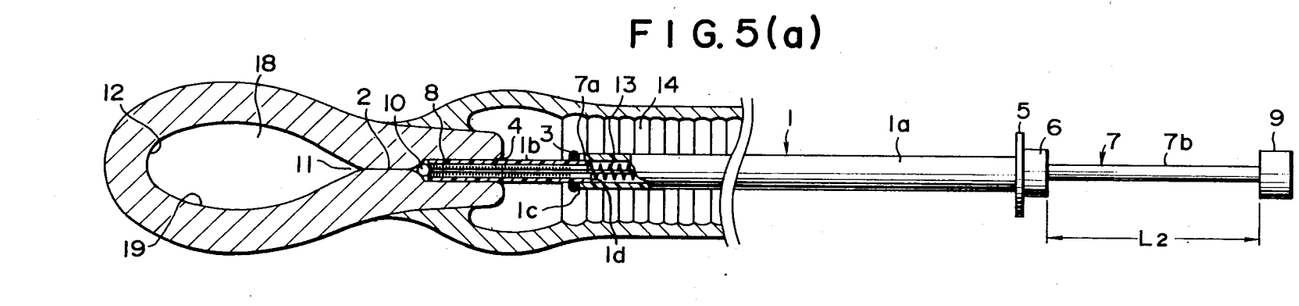
FIGS. 5a to 5e, shows cross sectional view of a uterus, a cervix, and a vagina and so on, with the endometrium cell sample collector according to the preferred embodiment of the present invention as shown in FIGS. 1 to 4 shown in various stages of taking an endometrium sample therefrom.

First, with no substantial force being applied to the knob or inward motion stop 9 on the outer end of the rod member 7, by gripping the outer portion of the larger diameter tube portion 1a, the left end of the device as seen in FIGS. 1 to 4 is inserted into the vagina 14, which at this time is typically dilated by the use of a speculum or the like, and the inward end of the device, i.e. the inward end of the smaller tube porton 1b and the inward end of the smaller rod portion 7a with the outward motion stop member 10 mounted thereon, is inserted into the external uterine os 4; the alignment necessary for this process may be done by ocular inspection, since the vagina 14 is dilated at this time, even if the angle of the cervix 2 should be awkward. Then, as shown in FIG. 5(a), the device is pushed inward by the operator, with the inward portion of the tube member 1, i.e. the smaller diameter tube portion 1b, sliding into the external uterine os 4; this is practicable even if the angle of the cervix 2 is awkward as mentioned above, because the smaller tube portion 1b and the smaller rod portion 7a are very flexible, as already explained. This process of insertion is continued until the elastic ring member 3 comes into contact with the external uterine os 4, as shown in FIG. 5a. This again may be checked by visual inspection, since the vagina 14 is dilated at this time. Thus the ring member 3 serves as a visual indication member for determining the proper depth of insertion of the device into the uterus. Beyond this point the device cannot be very easily inserted any further into the cervix 2, at least without the application of extra force, since the external diameter of the ring 3 is substantially greater than the diameter of the smaller diameter tube portion 1b, and as explained above typically is somewhat greater than the external uterine os 4. Because as mentioned above the distance $L_1$ between the inner end of the smaller diameter tube portion 1b and the side facing it of the ring 3 is slightly greater than the distance from the external uterine os 4 to the internal uterine os 11, i.e. the total length of the uterine os, at this stage of the utilization procedure the inner end of the device, i.e. the open inner end of the smaller diameter tube portion 1b with the outward motion stop member 10 abutted thereagainst, projects slightly into the uterine cavity 18 from the internal uterine os 11. During this insertion process, since the cell collection portion 8 on the rod member 7 is housed completely within the smaller diameter tube portion 1b, there is no risk of this cell collection portion 8 coming into contact with any part of the cervix 2 and undesirably removing cellular material therefrom, which would contaminate the sample of endometrium finally obtained; this is an important advantage of the present invention. The total length of the apparatus, and in particular of the tube member 1, is such that in the state shown in FIG. 5(b) the outer end of said tube member 1 is a few centimeters or so outside the body of the subject, as schematically shown in the figure.

Figure 5B:
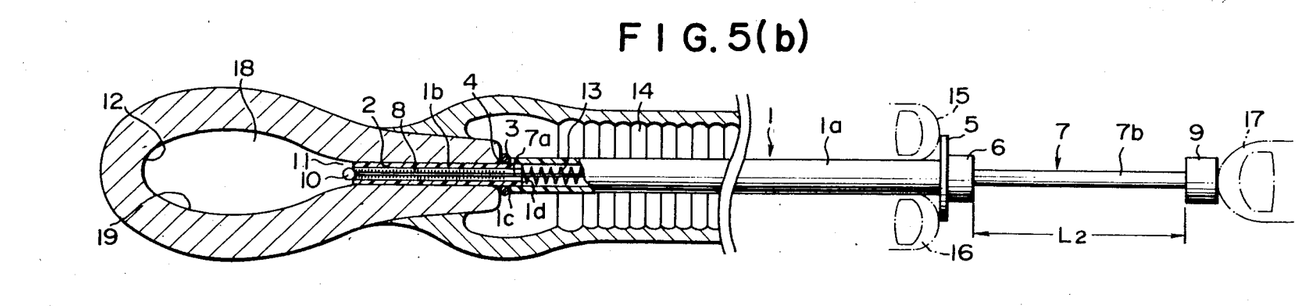
Figure 5C:
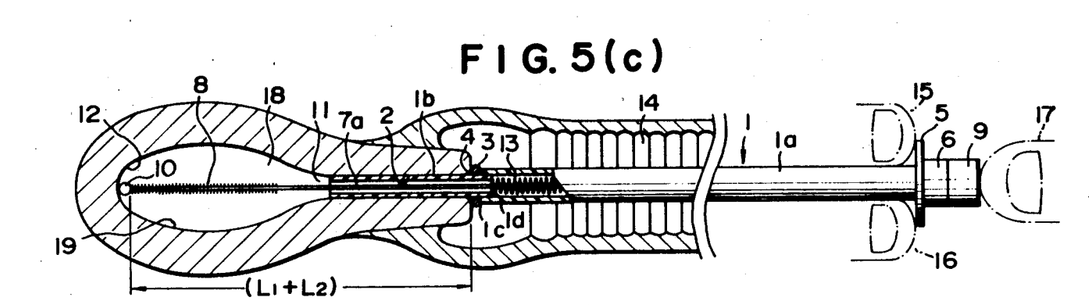

Next, with the outer tube member 1 maintained in position as shown in FIG. 5(b), the operator places his or her thumb 17 against the knob 9 on the outer end of the rod member 7, and places his or her index finger tip 15 and middle finger tip 16 on the two sides of the flange 5 mounted on the outward end of the larger tube portion 1a, as shown schematically in FIGS. 5(b) and 5(c) by the single dotted lines. This method of operation by using the digits of only one hand is very convenient, as will be readily apparent. Next, while keeping the outer tube member 1 substantially stationary in this position in this position (by in fact pushing it gently inwards, so as to keep the ring 3 abutted with a modest degree of force against the opening at the external uterine os 4), by squeezing his or her thumb 17 towards his or her finger tips 15 and 16 the operator pinches the knob 9 and the flange 5 towards one another, so as to push the rod member 7 in the leftwards direction in the figures relative to the outer tube member 1, against the biasing action of the compression coil spring 13 which is overcome, and so as to project the inward end of the smaller diameter portion 7a of said rod member 7 with the collection portion 8 and the outward motion stop member 10 thereon into the uterine cavity 18. This squeezing action by the operator is continued until, as shown in FIG. 5(c), the knob 9 and the collar 6 on the outward end of the larger diameter tube portion 1a are abutted against one another, so that the rod member 7 has been moved through its maximum stroke of length equal to $L_2$ in the leftwards direction in the figures relative to the outer tube member 1, and so that the collection portion 8 on the inward end of the rod member 7 is scraped gently against the endometrium 19. In fact, this scraping of the collection portion 8 against the endometrium 19 cannot be seen in FIG. 5(c), because said collection portion 8 is scraping against the sides of the uterus which lie out of the sectional plane of the drawing paper, more towards the viewer's eye and/or more away therefrom, but this is not visible in the figures. At this time, as shown in FIG. 5(c), the distance between the outward motion stop member 10 and the elastic ring 3 which is abutted against the opening of the external uterine os 4 is $L_1 + L_2$, and, since as mentioned above this distance $L_1 + L_2$ is approximately equal to the distance from the external uterine os 4 to the fundus 12 of the uterus, this scraping can be performed with complete safety and good gentleness, without any risk of damaging or puncturing the fundus 12 of the uterus with the outward motion stop member 10. The outward motion stop member 10 does not substantially interfere with the adhering of the portions of endometrium which are scraped off the uterus wall at this time to the collection portion 8, because it is of very small diameter, just large enough for it to fulfil its function as a stop member as explained above, and also to close the end of the smaller diameter tube portion 1b when pressed thereagainst as will be descanted upon later, as well as to provide a smooth ending member for the wires from which the smaller diameter rod portion 7a is wound, in order to ensure that the ends of these wires should not damage the uterus fundus 12.

Next, while still keeping the outer tube member 1 substantially stationary in its position so as to keep the ring 3 abutted against the opening at the external uterine os 4, by releasing this squeezing between his or her thumb 17 and finger tips 15 and 16, the operator allows the biasing action of the compression coil spring 13 to move the knob 9 and the flange 5 away from one another, so as to push the rod member 7 in the righwards direction in the figures relative to the outer tube member 1, and so as to pull the inward end of the smaller diameter portion 7a of the rod member 7 with the collection portion 8 thereon now hopefully bearing a sample of endometrium cells into the smaller diameter tube portion 1b, and so as to abut again the outward motion stop member 10 against the inward end of said smaller diameter tube portion 1b. Thereby the device and the hand of the operator are returned to the state shown in FIG. 5(b), wherein the rod member 7 has now been moved owtwards again through its maximum stroke of length equal to $L_2$ in the rightwards direction in the figures relative to the outer tube member 1. From this position, the above described pinching and releasing movements by the hand of the operator are repeated an appropriate number of times, until it is judged (on the basis of experience in the use of the device) that a satisfactory endometrium cell sample will have been collected on the collector 8.

Figure 5D:
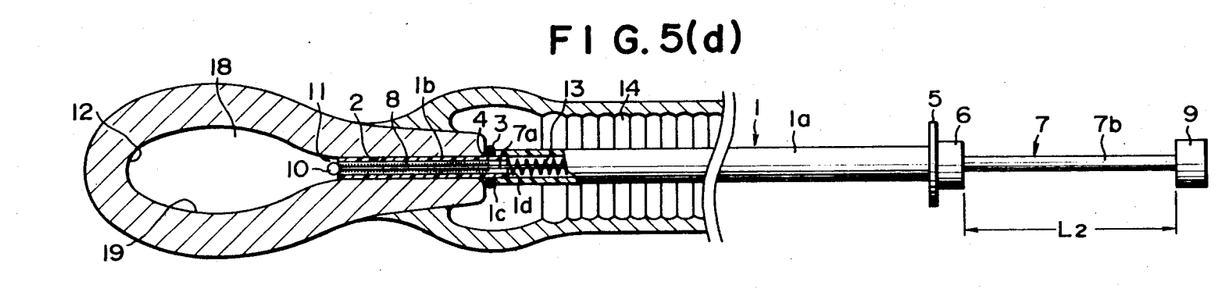

Finally, the device is withdrawn from the body of the subject, by the tube member 1 being pulled outward by the hand of the operator, so that first the inward portion of the tube member 1, i.e. the smaller diameter tube portion 1b, is slid out of the cervix 2, and subsequently the entire device with the endometrium cell sample collected thereby is withdrawn from the vagina 14. During this withdrawal process, it is very important that the knob 9 should be substantially released by the thumb 17 of the operator, so that under the biasing action of the compression coil spring 13 the rod member 7 is moved to its maximum extent in the rightwards direction in the figures relative to the outer tube member 1, and so that the inward end of the smaller diameter portion 7a of the rod member 7 with the collection portion 8 bearing the required sample of endometrium cells on it is completely housed inside the smaller diameter tube portion 1b, and so as to abut the outward motion stop member 10 against the inward end of said smaller diameter tube portion 1b, thus closing said inward end of said smaller diameter tube portion 1b. This released state for the knob 9 is shown in FIG. 5(d); the endometrium cell sample is not shown in this figure because it is difficult to represent graphically. By this protection of the endometrium cell sample which has been taken by housing it inside the smaller diameter tube portion 1b, it is effectively prevented from becoming contaminated by cervical or vaginal cells, as the device is withdrawn from the body of the subject.

Figure 5E:
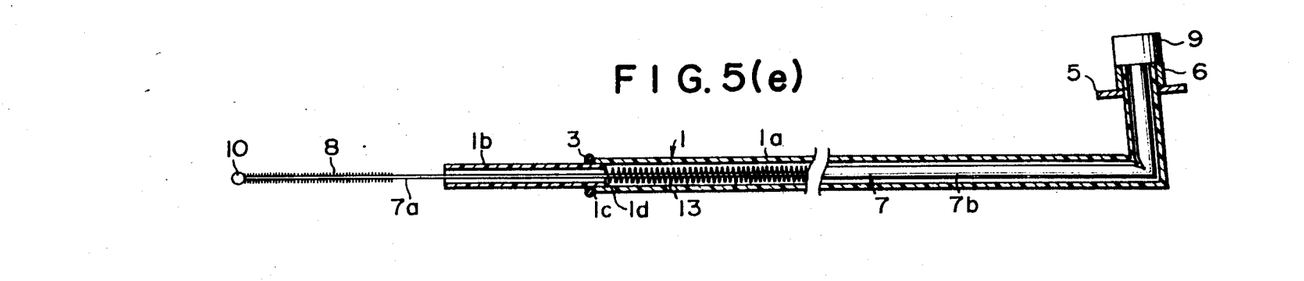

When the device has been withdrawn from the body of the subject, and has been transported to a suitable place for removal of the endometrium cell sample taken thereby and held on the collector portion 8, the knob 9 is once again squeezed by the operator towards the flange 5 so as to project the inward end of the rod member 7 and the collector portion 8 out of the smaller diameter tube portion 1a, so that the endometrium cell sample can be accessed for removal. In the event that the device according to the present invention is a disposable type device, which is not an essential feature of the present invention but is a useful specialization thereof which is incorporated in the shown preferred embodiment, then as shown in FIG. 5(e) conveniently the larger diameter tube portion 1a and the larger diameter rod portion 7b passing therethrough may be bent through a substantial angle, while keeping the knob 9 and the flange 5 squeezed together as explained above, so as to fix the rod member 7 with respect to the tube member 1 and prevent it sliding therein ever again, and so as thus to prevent the biasing action of the compression coil spring 13 from being able to pull back the collector portion 8, etc., into the smaller diameter tube portion 1b. This specialized operation of the shown preferred embodiment is very helpful for aiding with removal of the endometrium cell sample, because thereafter it is no longer required that the operator should continue to pinch the knob 9 and the flange member 5 towards one another, and accordingly the operator is able subsequently to concentrate on the task of properly removing the endometrium cell sample from the collector portion 8. Of course, this bending and fixing operation requires that either the larger diameter tube portion 1a or th larger diameter rod portion 7b should be made of a non elastic material which can readily be plastically deformed—in the shown preferred embodiment, it is the larger diameter rod portion 7b which is thus made plastically deformable, being made of aluminum alloy tube as stated above.

This concludes the description of the operation of this device. As the endometrium sample collected by the device of the present invention is obtained not by such an unreliable method as the suction method used in the prior art, but by physically scraping the inner lining of the uterus, thereby it is positively and effectively removed, and no doubt exists as to the certainty of quickly and easily obtaining a satisfactory endometrium cell sample. Further, since the inward motion of the tube member 1 in toward the uterine cavity 18 is limited by observation of when the ring 3 comes into contact with the external uterine os 4, and since the inward motion of the rod member 7 with respect to the tube member 1 is limited by the knob 9 which also functions as a stop member coming into contact with the collar 6 and/or the outer end of the larger diameter tube portion 1a, thus it is satisfactorily ensured that the depth of penetration of the extreme tip of the rod member 7, i.e. of the outward motion stop member 10, into the uterine cavity from the external uterine os 4, does not exceed the distance of $L_1+L_2$. Thereby it is ensured that no risk is run of damage to the cervix or the uterus.

Because this preferred embodiment of the endometrium cell sample collector of the present invention can be operated, as explained above, by only one hand, it is very convenient and easy of use. This effect is largely obtained by the provision of the compression coil spring 13 for biasing the rod member 7 in the outward direction with respect to the tube member 1, so that, when the cell collection portion 8 is required to be withdrawn and to be accomodated in the interior space within the smaller diameter tube portion 1b, there is no need to pull the rod member 7 outwards with respect to the tube member 1 manually. At this time, because by this biasing action of the compresion coil spring 13 the outward motion stop member 10 is pulled against the inner end of the smaller diameter tube portion 1b, therefore during removal of the device with the endometrium cell sample taken thereby held on the collector portion 8, this cell sample is housed securely within the smaller diameter tube portion 1b, the inner end of which is closed at this time by said outward motion stop member 10, and accordingly no risk is run of undesirable contamination of the sample of endometrium cells taken by the device with any cells from the cervix or vagina. This is an important advantage of the shown preferred embodiment of the present invention.

Because, as in the shown preferred embodiment, the endometrium cell sample collector of the present invention can be made cheaply enough to be disposable, thereby it is not required to be cleaned for reuse at any time, and thereby there arise no problems with cleanliness or sterilization during use. Also the use of such a disposable device is inherently economical of labor, and accordingly is cheap. Because no parts of the endometrium cell sample collector of the present invention are required to form airtight seals against one another, in contrast to the form of prior art mentioned in which a suction device is employed, the manufacturing accuracy required for the parts of the endometrium cell sample collector of the present invention is low, which further aids in keeping costs low. Further, in the case of a disposable version of the present invention which as stated above is preferred, because as explained with reference to FIG. 5(e) the outer portion of the device can be permanently bent through a sharp angle to prevent the inner rod member from ever again moving with respect to the outer tube member, the process of removal of the endometrium cell sample is made easy.

As a further advantage of the shown preferred embodiment of the present invention, since as explained above both the inward smaller diameter tube portion 1b and also the inward smaller diameter rod portion 7a are made as quite flexible, thereby no only is the risk of damaging the vagina, the cervix, or the uterus during insertion of the device further minimized, but also the insertion process is aided. This is particularly so in the case that the angle of the cervix of the particular female subject in question is awkward, and could of course be done by making the whole of the rod member flexible. Now, in this case of such an awkwardly angled cervix, a further particular advantage of the shown preferred embodiment of the present invention is that, because the inward smaller diameter rod portion 7a is made of a pair of twisted metallic wires, which can be elastically deformed easily by being bent at a certain radius of curvature, but which can be thereafter plastically deformed by being bent at a smaller radius of curvature than said certain radius, therefore it is possible, before insertion of the device into the vagina of the subject, to bend the tip portion of the device including the smaller diameter rod portion 7a (which itself is thus at this time plastically deformed into a new shape which it assumes with a certain degree of tenacity) and the smaller diameter tube portion 1b (which is at this time held in a bent shape by the thus plastically deformed smaller diameter rod portion 7a) to such a convenient shape as can be easily inserted at this awkward angle into the uterine os of this particular subject. This particular advantage of the present invention would not be available in the case that this smaller diameter rod portion 7a were made of such a material as, for example, ordinary synthetic resin, which does not easily undergo such plastic deformation.

Now, in the case of a female subject the length of whose cervix 2 is substantially greater than the average, then as will be understood based upon the foregoing explanations the length of the smaller diameter tube portion 1b will prove insufficient for removal of a proper endometrium cell sample in the manner described above, and also there is a risk that during the reciprocating action of the rod member 7 in order to gather the endometrium cell sample as described above the collector portion 8 on the inward end thereof will come into contact with an scrape against the cervical cells lining the internal uterine os 11, which will contaminate the endometrium cell sample and cause difficulties with regard to use thereof. However, a modified method of use for the preferred embodiment of the present invention described above may be practiced, as follows. Before insertion of the device into the vagina, by the application of a moderate force in an outward direction (rightwards in the figures) the ring 3 may be be pushed from the smaller tube portion 1b past the outer step 1c over the larger tube portion 1a and along it for a certain distance, and as explained previously if this is done the ring 3 cannot thereafter slide on the larger diameter tube portion 1a very easily, but is quite firmly fixed thereon with respect to the longitudinal direction. Thereby the magnitude of the distance $L_1+L_2$ between the inward end of the rod member 7 and the inward facing side of the ring 3 may be increased, which increases the maximum distance of easy penetration of said inward end of the rod member 7 into the uterine cavity 18, thus allowing for the extra length of the cervix of this particular subject. This can only be effective, of course, provided that the diameter of the larger tube portion 1a is small enough for said larger diameter tube portion 1a to be able to be slipped through the external uterine os 4 of the cervix 2, at least in the case of such a cervix which is somewhat longer than the normal cervix, and therefore may be expected to have an external uterine os of a somewhat greater diameter.

In the shown preferred embodiment, the cell collector portion 8 is formed as a brush, but this is not intended to be limitative of the present invention, since other forms for an efficient cell collector portion could be conceived of, which would be efficient for endometrium cells to adhere to, once they came into contact therewith. Further, the means for preventing the inward motion of the rod member 7 relative to the tube member 1 from proceeding past a predetermined relative point, which in the shown and described preferred embodiment comprises the knob 9 which in addition is used for pushing the rod member 7 inwards, could be realized in another manner, and is not required to incorporate such a knob type function, or to be provided at the outward extremity of the device. Similarly, the means for preventing the outward motion of the rod member 7 relative to the tube member 1 from proceeding past a predetermined relative point, which in the shown preferred embodiment comprises the stop 10 which in addition is used for closing the inner end of the outer tube 1, could also be realized in another manner, and is not required to incorporate such a closing function, or to be provided at the inward extremity of the device. Therefore, although the present invention has been shown and described with reference to a preferred embodiment thereof, and in terms of the illustrative drawings, it should not be considered as limited thereby. Various possible modifications, omissions, and alterations could be conceived of by one skilled in the art to the form and the content of any particular embodiment, without departing from the scope of the present invention; and therefore it is desired that the scope of the present invention, and of the protection sought to be granted by Letters Patent, should be defined not by any of the perhaps fortuitous details of the shown embodiment, or of the drawings, but solely by the scope of the appended claims, which follow.

What is claimed is:

1. A method of collecting a sample of endometrium cells from the uterus of a subject, comprising:
    providing a collector, said collector comprising:
    (a) a tube member, formed with a central axially extending aperture, and comprising an inward portion, with an inward free end, at least an inward end part of which including said inward free end thereof is flexible, and a substantially coaxial outward portion axially abutted thereto with a free end;
    (b) a rod member, which is passed at least partly through said central axially extending aperture of said tube member, comprising and inward portion, with an inward free end, which is flexible, and a substantially coaxial outward portion axially abutted thereto with a free end;
    (c) a means for collecting endometrium cells, provided on said inward portion of said rod member near its said free end;
    (d) a means for biasing said rod member with respect to said tube member in the outward direction;
    (e) a means for preventing said rod member from moving with respect to said tube member in the outward direction past a first certain point at which said endometrium cell collecting means is completely housed within said inward portion of said tube member; and
    (f) a means for preventing said rod member from moving with respect to said tube member in the inward direction past a second certain point at which said endometrium cell collecting means projects from said free end of said inward portion of said tube member;
    inserting said collector into the cervix of the subject whereby the inward portion of said tube member is inserted into the uterine cervix of the subject until said inward free end is slightly past the internal uterine os;
    applying a force to the collector to reciprocate said rod member in said tube member in the inward and outward directions, said force alternately respectively overcoming and being overcome by the biasing action of said biasing means between said first and second certain points to alternately project said endometrium cell collecting means from said inward free end of said tube member whereby because of the flexibility of the rod member, said means for collecting endometrium cells can be readily placed in contact with the walls of the uterus to scrape endometrium cells of the wall of the uterine cavity of the subject;
    withdrawing said endometrium cell collecting means into said inward portion of said tube member so that the rod member is positioned at said first certain point with respect to the tube member and the endometrium cell collecting means is completely housed within said inward portion of said tube member; and
    withdrawing the collector from the cervix of the subject.

* * * * *